(12) United States Patent
Woo et al.

(10) Patent No.: US 10,507,269 B2
(45) Date of Patent: *Dec. 17, 2019

(54) CATHETER LOCK SOLUTION FORMULATIONS

(71) Applicant: Medline Industries, Inc., Northfield, IL (US)

(72) Inventors: Lecon Woo, Libertyville, IL (US); William Anderson, Cary, IL (US)

(73) Assignee: Medline Industries, Inc., Northfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/373,850

(22) Filed: Apr. 3, 2019

(65) Prior Publication Data

US 2019/0224385 A1    Jul. 25, 2019

Related U.S. Application Data

(63) Continuation of application No. 14/554,018, filed on Nov. 25, 2014, now Pat. No. 10,300,176.

(60) Provisional application No. 61/908,438, filed on Nov. 25, 2013.

(51) Int. Cl.
*A61L 33/04*     (2006.01)
*A61L 29/14*     (2006.01)
*A61L 29/16*     (2006.01)
*A61L 33/00*     (2006.01)

(52) U.S. Cl.
CPC ............... *A61L 33/04* (2013.01); *A61L 29/14* (2013.01); *A61L 29/16* (2013.01); *A61L 33/0005* (2013.01); *A61L 2300/404* (2013.01); *A61L 2300/406* (2013.01); *A61L 2300/42* (2013.01)

(58) Field of Classification Search
None
See application file for complete search history.

(56) References Cited

U.S. PATENT DOCUMENTS 9,457,002 B2 * 10/2016 Raad ...................... A61K 45/06
10,300,176 B2 * 5/2019 Woo ........................ A61L 33/04

* cited by examiner

*Primary Examiner* — Dale R Miller
(74) *Attorney, Agent, or Firm* — Fitch, Even, Tabin & Flannery LLP

(57) ABSTRACT

A liquid excipient is added to a lock solution formulation containing a lower alcohol and an anti-coagulant, antibiotic, and/or anti-microbial, such as the ethanol and tri-sodium citrate lock solution formulation, to prevent citrate from crystallizing in catheters made from silicone. The locking solution could include a liquid excipient, such as glycerol, polysorbate-20, or polyethylene glycol (PEG)-400, along with a lower alcohol, such as ethanol, and an anti-coagulant, such as tri-sodium citrate, antibiotic, and/or anti-microbial.

18 Claims, 4 Drawing Sheets

CATHETER LOCK SOLUTION FORMULATIONS

CROSS-REFERENCE TO RELATED APPLICATIONS

The present application is a continuation of U.S. application Ser. No. 14/554,018, filed Nov. 25, 2014, which claims the benefit of U.S. Provisional Application Ser. No. 61/908,438 filed Nov. 25, 2013. The prior provisional application is incorporated herein by reference in its entirety.

FIELD

The present disclosure relates to locking solutions for a catheter, and more particularly to locking solutions that prevent occlusion.

BACKGROUND

Implanted catheters enjoy widespread use in a number of medical procedures. For example, intravenous (IV) therapy relies on long-term implantation of a venous catheter to deliver fluids, medications, and other substances to a patient. Hemodialysis and hemofiltration both rely on separate draw and return catheters implanted in a vein to allow extracorporeal treatment of the blood. Peritoneal dialysis, in contrast, relies on a single catheter implanted in the peritoneum to permit introduction and withdrawal of dialysate to permit in situ dialysis.

The need to leave catheters implanted over long periods of time raises a number of concerns. For example, the catheters can become infected requiring treatment of the patient and often times removal of the catheter. This is a particular problem with transcutaneous catheters where the skin penetration is a common route of infection. In addition, implanted catheters can often become plugged or fouled over time. This is a particular problem with intravascular catheters where clotting and thrombus formation within the catheter lumen can be problematic.

To reduce problems associated with thrombus formation and to maintain the patency of catheters, it is now common to "lock" catheters between successive uses. Locking typically involves first flushing the catheter with saline to remove blood and other substances from the catheter lumen. After the catheter has been flushed, an anti-coagulant solution, such as heparin, is then injected to displace the saline and fill the lumen. The heparin-locking solution both excludes blood from the lumen and actively inhibits clotting and thrombus formation within the lumen. While some thrombus may still form at the distal tip of the catheter, the formation is usually minimal. It has further been proposed to combine various anti-microbial, bactericidal, or bacteriostatic substances with the locking solution in order to inhibit infection at the same time that thrombus is being inhibited.

While generally effective, the use of heparin locks suffers from a number of disadvantages. The need to prepare a heparin solution at the end of every catheter treatment session is time-consuming and presents an opportunity for a caregiver to commit an error. Hemodialysis and hemofiltration patients will have to undergo such heparin locks at least several times a week, while patients on IV may have to undergo such heparin locks several times a day. Over time, heparin locks are inconvenient and expensive. Moreover, the need to combine a separate anti-microbial agent in the heparin lock solution further complicates the procedure and adds expense, and the addition of an anti-microbial agent to the heparin lock will generally be effective only within the lumen and at the openings from the lumen. There will be little reduction in the risk of infection in the regions surrounding the implanted catheter, including at the point of penetration through the skin where the risk of infection is the greatest.

A lock solution formulation containing ethanol and tri-sodium citrate provides anti-coagulant and disinfection properties. However, catheters made with silicone elastomers, due to their very high moisture and alcohol permeability, as well as catheters made of other permeable materials, could become blocked due to crystallized citrate lodged in some segments of the catheters, causing occlusion.

It would be desirable to improve lock solution formulations containing a lower alcohol and an anti-coagulant, antibiotic, and/or anti-microbial, such as the ethanol tri-sodium citrate formulation, to prevent such blocking while maintaining their performances.

SUMMARY

The present disclosure provides solutions for improved locking and/or disinfection of catheters. Excipients are added to a lock solution formulation containing a lower alcohol and an anti-coagulant, antibiotic, and/or anti-microbial, such as the ethanol and tri-sodium citrate lock solution formulation, to prevent citrate from crystallizing in catheters made from silicone.

The locking solution could include a liquid excipient, such as glycerol, polysorbate-20, or polyethylene glycol (PEG)-400, along with a lower alcohol, such as ethanol, and an anti-coagulant, such as tri-sodium citrate, antibiotic, and/or anti-microbial.

In one aspect, the locking composition for a catheter includes at least one lower alcohol, at least one anti-coagulant compound, and at least one liquid excipient at a sufficient concentration to minimize the at least one anti-coagulant compound from crystallizing. In another aspect, a locking composition for an implantable silicone catheter includes a lower alcohol, an anti-coagulant compound, and an excipient, wherein the excipient is present in the amount of at least about 0.5% by weight of the locking composition.

In another aspect, a method of preventing crystallization in an implantable silicone catheter is provided. The method includes introducing a locking composition into a lumen of the implantable silicone catheter, wherein the locking composition includes a lower alcohol, having one to four carbon atoms, an anti-coagulant compound, and an excipient, wherein the excipient is present in the amount of at least about 0.5% by weight of the locking composition.

BRIEF DESCRIPTION OF THE DRAWINGS

The foregoing features of the present disclosure will be apparent from the following Detailed Description, taken in connection with the accompanying drawings, in which.

DETAILED DESCRIPTION

Figure 1:
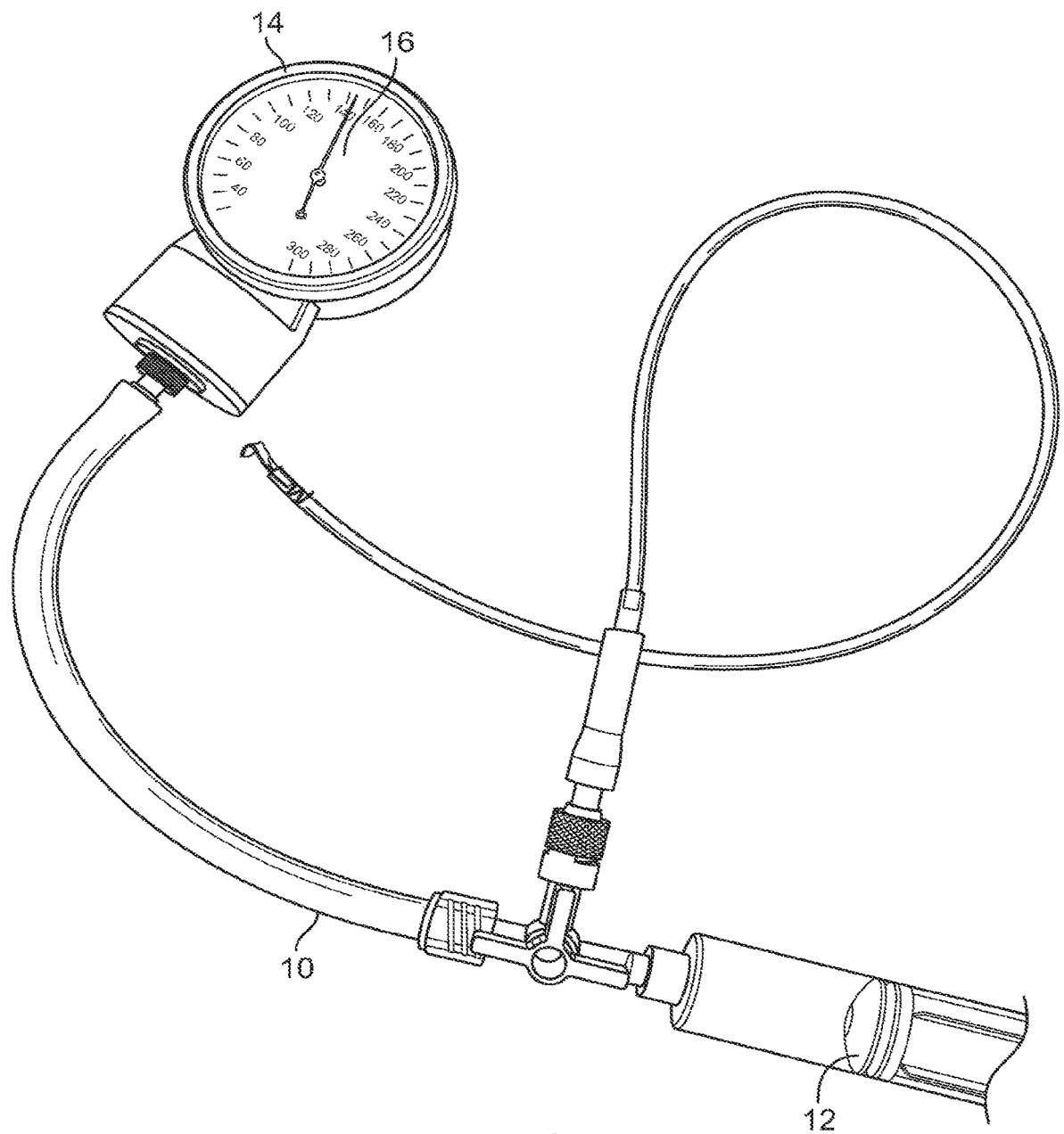
FIG. 1 shows a sphygmomanometer connected to a syringe.

The present disclosure is directed to catheter lock solutions including a lower alcohol combined with a functional compound such as an anti-coagulant, antibiotic, and/or antimicrobial; and an excipient. The catheter lock solution could include ethanol, tri-sodium citrate, and an excipient. The term "lock solution," as used herein, refers to a solution that is introduced (e.g., injected) into a lumen of a catheter and is, at least partially, allowed to remain in the lumen until access to the lumen is needed. Generally, such solutions provide anti-coagulant and antibacterial properties to an implanted catheter as the solution remains in the catheter between uses.

The lower alcohol is effective in inhibiting fouling, plugging, and infection of the lumen of indwelling catheters. As used herein, the term "lower alcohol" refers to an alcohol having one to four carbon atoms. Exemplary lower alcohols include, but are not limited to, ethanol, propanol, isopropanol, butanol, and combinations thereof.

Exemplary anticoagulants include, but are not limited to, riboflavin, sodium citrate, ethylene diamine tetraacetic acid, heparin, low molecular weight heparin, citric acid, etc. Exemplary antimicrobials include, but are not limited to, taurolidine, triclosan, chlorhexidine, etc. Exemplary antibiotics include, but are not limited to, gentamicin, vancomycin, etc.

A lock solution containing a lower alcohol and an anticoagulant is disclosed in U.S. Pat. No. 6,685,694, the disclosure of which is incorporated herein by reference in its entirety. The entire disclosures of related U.S. Pat. Nos. 6,592,564 and 6,679,870 are also incorporated herein by reference.

The excipient could be any suitable agent that upon addition to a lower alcohol, such as ethanol, and an anticoagulant, such as tri-sodium citrate, antibiotic, and/or antimicrobial, prevents or minimizes the functional compound from forming a plug or occluding or crystallizing in catheters made from silicone or other permeable materials such as rubber (dimethylsilicone rubber, nitrile rubber, and natural rubber). By occluding what is meant is a blockage in flow through a catheter that requires a pressure of more than 150 mmHg on a typical 10 cc syringe to overcome the blockage. This is equal to about 0.9 lbs. of force on the syringe plunger. It is preferable that a blockage can be overcome with a pressure of less than 100 mmHg. This is equal to about 0.6 lbs. of force on the syringe plunger. It is more preferable that a blockage can be overcome with a pressure of less than 50 mmHg, and even more preferable that a blockage can be overcome by a pressure of 20 mmHg or less, which is not a readily noticeable amount of pressure. Such agents include certain liquid excipients that were found to be effective based on experiments, which involve measuring a pressure or vacuum level in millimeters of mercury (mmHg), as described in further detail below. The pressure or vacuum level, referred to as the break through pressure or vacuum level, provided a quantitative measure of the formulation performance in preventing plug formation. The liquid excipients that were found to be effective based on experiments at the 2% by weight level include, but are not limited to, glycerol, polysorbate-20, and PEG-400. The data $P_{break-through}$ was less than 10 mmHg (pressure and vacuum) for these excipients.

Other excipients could be effective at the 2% by weight level. These excipients include, but are not limited to, PEG-100, PEG-200, PEG-300, Triton X-100 (t-octylphenoxypolyethoxyethanol), Polysorbate-80, Poloxomer 124, Macrogol 15 Hydroxy Stearate, Cremophor EL (Polyoxyl 35 Castor oil), and other suitable water soluble non-ionizing liquid excipients.

Excipients could be effective at approximately the 1% by weight level. These excipients include, but are not limited to, Glycerol (conditionally acceptable, free flowing for greater than 7 days), Polysorbate-20 (similar to Glycerol), and Triton X-100.

A combination of excipients could be effective in an amount less than 2% by weight level in total. These excipients include, but are not limited to, 1% Glycerol combined with 0.5% Polysorbate-20 (estimated to be one of the most effective-reduced excipient concentration and performance assurance), 1% Glycerol combined with 0.5% Triton X-100, 0.75% Glycerol combined with 0.75% Polysorbate-20, and 0.5% Glycerol combined with 0.5% Polysorbate-20.

FIG. 1 is a view of a sphygmomanometer 10 connected to a syringe 12. The sphygmomanometer 10 includes a gauge 14 with a visual display 16 to measure the pressure or vacuum level. The sphygmomanometer 10 and the syringe 12 were used to measure the break through pressure or vacuum level.

Experiments

Long silicone rubber commercial catheter extension tubing segments spliced together, or a single small bore with a 1.5 mm inner diameter clear, and very soft laboratory silicone rubber tubing of about 15 inch in length were used for evaluation. Formulations of 30% weight per volume (w/v) ethanol and 4% weight per weight (w/w) tri-sodium citrate with candidate biocompatible excipients were prepared and charged into the lumens of simulated catheter tubings and capped with solid plugs. The samples were first dried near a de-humidifier for about 24 hours to allow evaporation of most ethanol before being placed into a clear polycarbonate drying column connected in series with a large Drierite® desiccant column. The columns were also fitted with a gas flow meter and a diaphragm gas pump to provide closed loop gas circulation at about 4 liter per minute (min-l). In this manner, the vertically placed model catheter segments were subjected to a gas stream of near zero humidity and any moisture escaped from the tubing was swept away by the flowing air stream and immediately captured by the desiccant. From time to time, when a near solid plug was observed, the sample was removed from the column. Both the pressure (+) or vacuum (−) levels to cause the liquid or solid plug movement were measured when subjected to actuation movements from a small air filled syringe 12 connected to a sphygmomanometer 10. These levels are referred to as the break through pressure or vacuum levels.

When the concentrated plug is in the liquid state, very slight pressure or vacuum level, less than 5 mmHg, caused visible movements of the plug for dislodging. However, when the solution containing segments are condensed into a semi-solid gel-like plug, pressure or vacuum levels of much greater than 100 mmHg were required for dislodging.

Results and Discussion

Among the many water soluble and biocompatible excipients evaluated, it was determined that solid excipients at times formed gel-like plugs, which required high break through pressures to dislodge the plugs.

Figure 2:
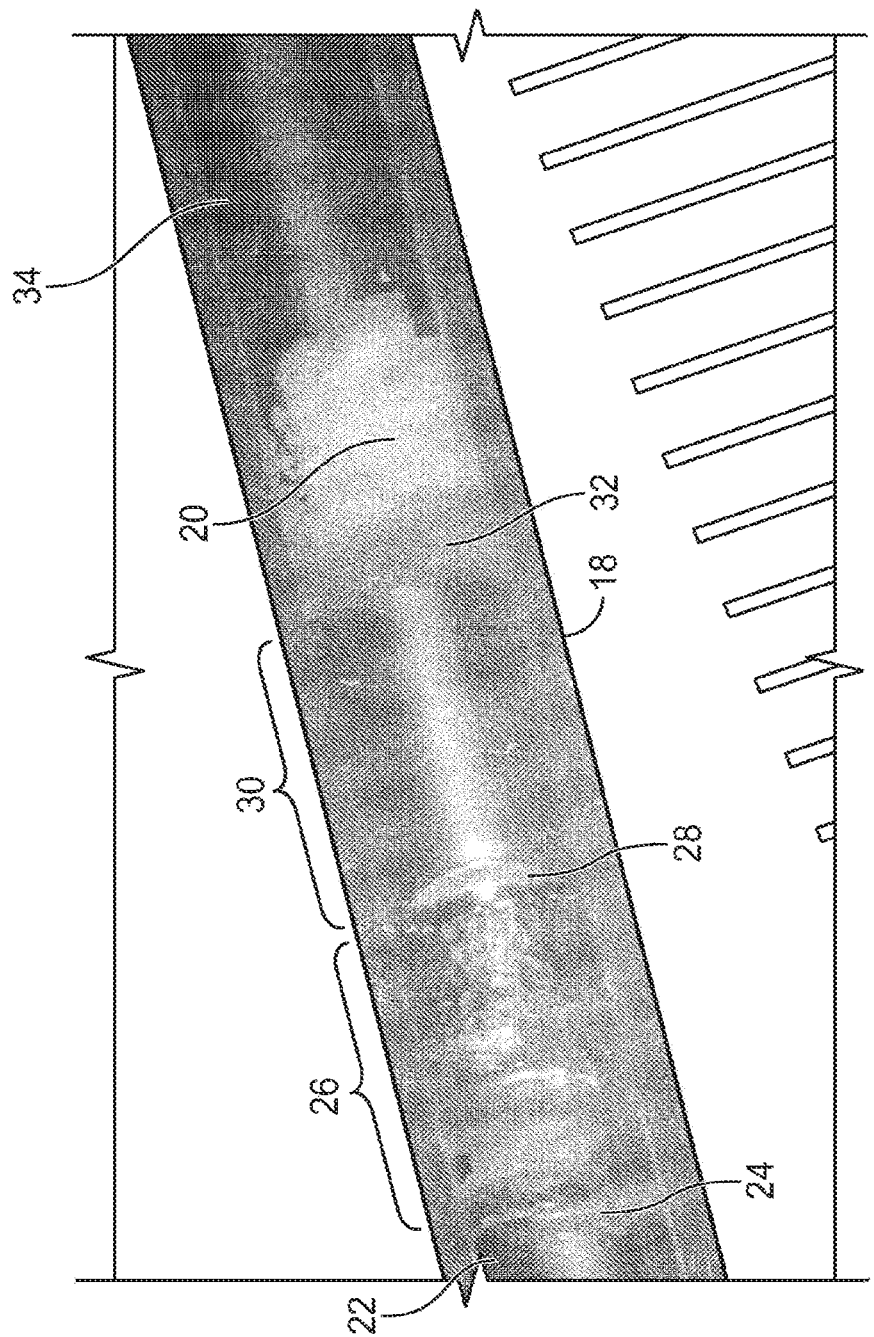
FIG. 2 shows a catheter tubing with a gel-like plug.

The results of an experiment performed with solid excipients are shown in FIG. 2. In particular, FIG. 2 is a view of a catheter tubing 18 with a gel-like plug (crystallized sodium citrate) 20. A void 22 is left due to evaporation and permeation of ethanol through the catheter tubing 18. FIG. 2 shows the edge 24 of the crystallization of the gel plug 26, which is a highly viscous and is formed due to highly concentrated sodium citrate that has not fully crystallized. The meniscus 28 of the fluid line is adjacent the gel plug 26. Fluid 30 is trapped between the gel plug 26 and the crystallized sodium citrate 20. A wetted portion 32 of the sodium citrate crystal is located adjacent to another void 34 from evaporation of ethanol. The gel-like plug 20 was formed from a solution of 30% ethanol, 4% sodium citrate, 2% polyethylene glycol-3350 (PEG-3350) and 0.1% polysorbate-80 (PS-80). The break through pressure or vacuum level exceeded 140 mmHg.

Excipients which are liquid at room temperature could be quite effective alone or in combination with another liquid excipient with surfactant properties. In addition, surprisingly, at rather low concentrations below that of the tri-sodium citrate, certain excipients which are liquid at room temperature appeared to retard or inhibit the tri-sodium citrate from crystallizing, making the resulting formulation flowable even after exhaustive drying.

Figure 3:
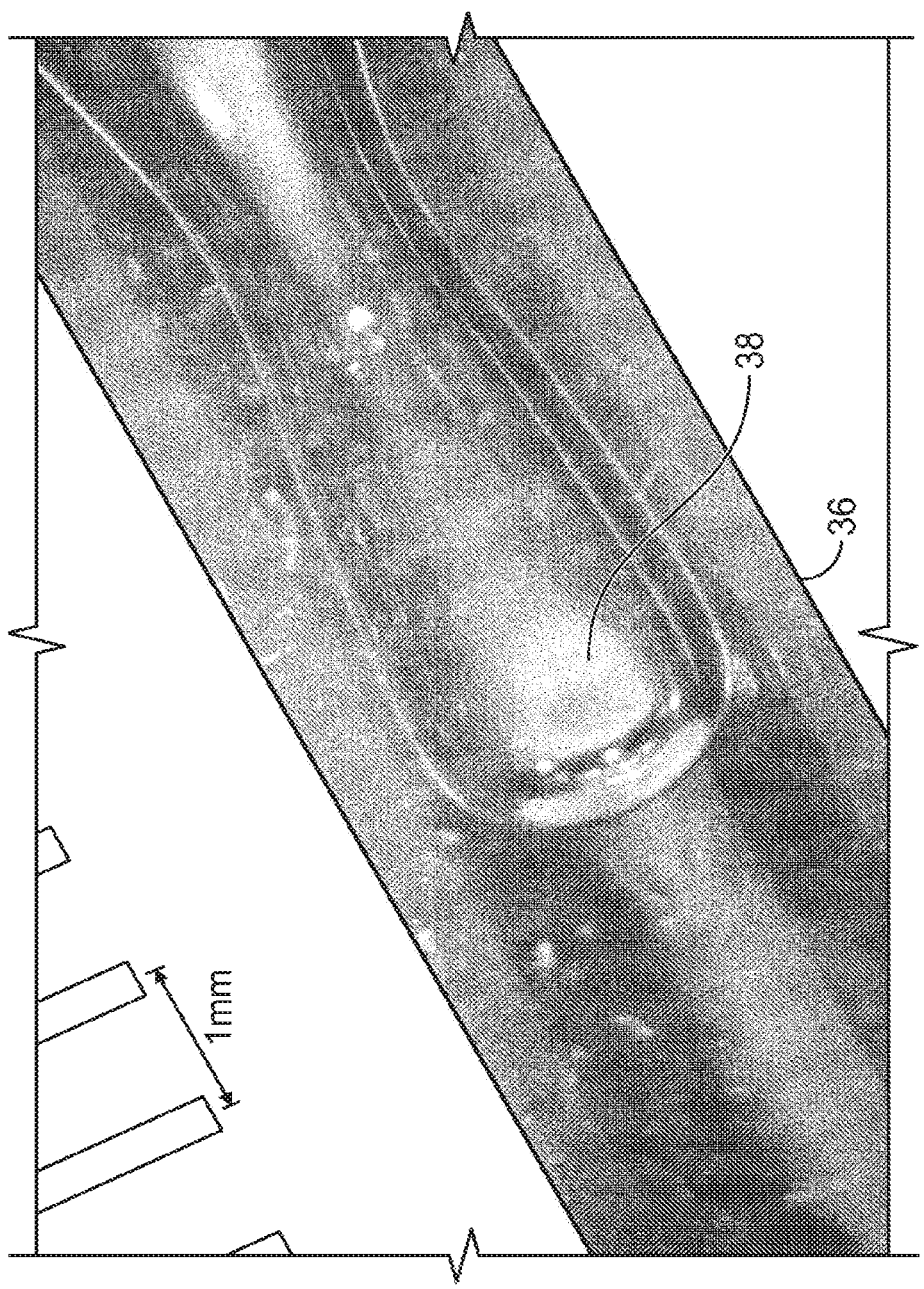
FIG. 3 shows a catheter tubing with a recoiling liquid/bubble.

The results of an experiment performed with liquid excipients are shown in FIG. 3. FIG. 3 is a view of a catheter tubing 36 with a recoiling liquid/bubble 38 or recoiling air/liquid interface. An antiseptic locking solution containing 30% ethanol and 4% sodium citrate, and 2% Polysorbate-20, was subjected to rigorous drying for 12.5 days, yet remained completely fluid, and formed the recoiling liquid/bubble 24. This illustrates the effectiveness of a formulation with Polysorbate-20.

To test the hypothesis for excipients that can prevent gelation based on hydrophobic interaction with the silicone surface, we develop two new lock formulations that include excipients Polysorbate 80 and Pluronic F68, respectively:

A. 30% ethanol, 4% sodium citrate, with Polysorbate 80 with two concentrations: 0.2% and 0.7%.

B. 30% ethanol, 4% sodium citrate, with Pluronic F68 with two concentrations: 0.2% and 0.7%.

Figure 4:
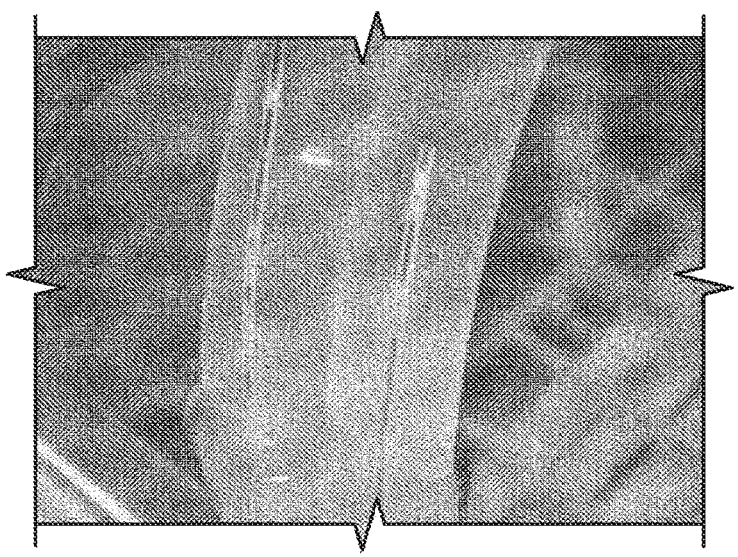
FIG. 4 shows a Groshong 4Fr catheter after 1 day.
Figure 5:
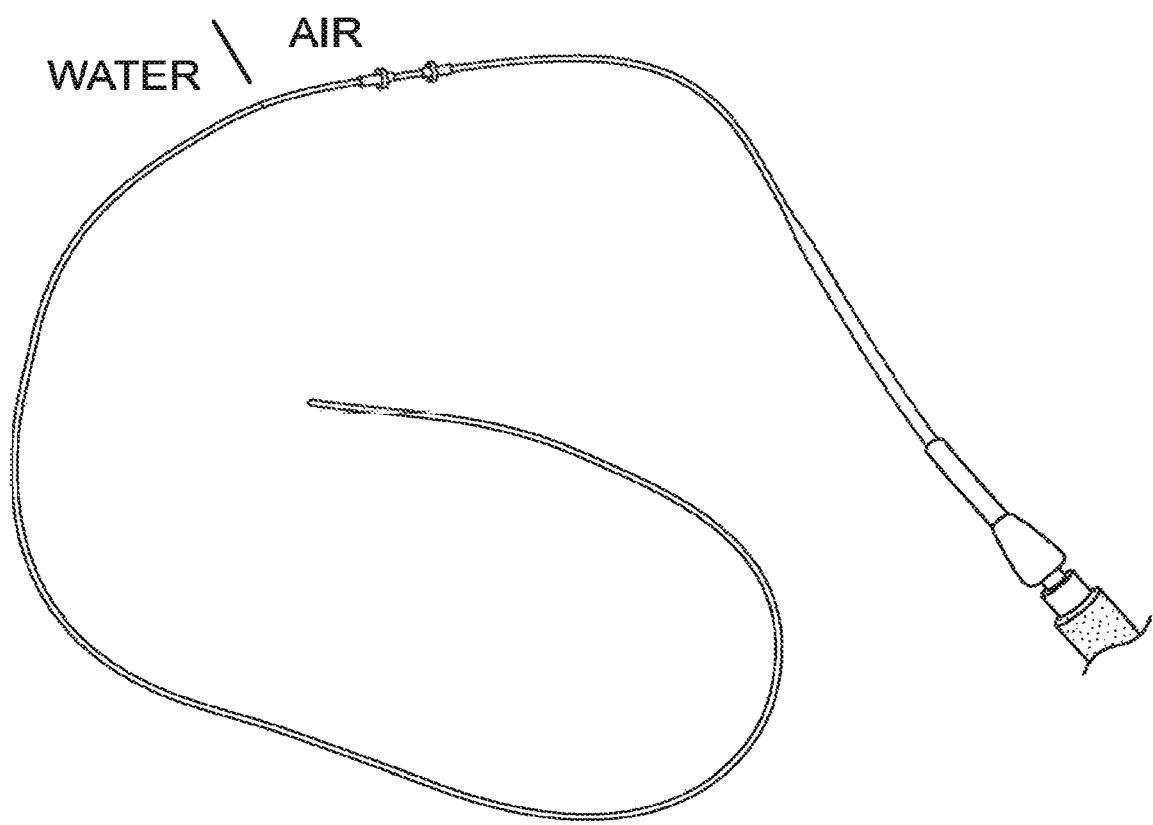
FIG. 5 shows a Groshong 4Fr catheter after 14 days.

When Groshong 4Fr catheters were filled with 30% ethanol, 4% sodium citrate, with 0.7% Polysorbate 80 and 30% ethanol, 4% sodium citrate, with 0.7% Pluronic F68 and tested for a period of 14 days, a lot of voids/gas bubbles were observed in the first days (FIG. 4). The question was what are the bubbles and do they affect the occlusion of the catheter. Gas bubbles were observed in all three Groshong catheters filled with 30% ethanol, 4% sodium citrate, with 0.7% Polysorbate 80, and 30% ethanol, 4% sodium citrate, with 0.7% Pluronic F68, respectively, in the in vitro aqueous bath with vascular flow simulation. After 14 days there were no voids/bubbles in the segment of the catheter immersed into the water and the solution line was continuous, while the whole dry segment was empty (FIG. 5).

An in vitro test evaluated catheter lock formulations containing 0.2% additives: 30% ethanol, 4% sodium citrate, with 0.2% Polysorbate 80, and 30% ethanol, 4% sodium citrate, with 0.2% Pluronic F68. There were no voids/gas gaps when Per-Q-Cath 4F catheters were subjected to in vitro simulation bath for 12 days without changing the solution. Catheters with 30% ethanol, 4% sodium citrate, with 0.2% Polysorbate 80, and 30% ethanol, 4% sodium citrate, with 0.2% Pluronic F68, and a lock solution of 30% ethanol, 4% sodium citrate with 0.5% Polysorbate 20 and 1% of Glycerol had <20 mmHg pressure after 12 days in vitro in water bath @37° C. These formulations had better performance than lock solution without excipients (control). Per-Q-Cath catheters filled with the control lock solution at pressure greater than 300 mmHg when subjected to the same conditioning.

Based on the results from the preliminary in vitro study of Groshong 4Fr and Per-Q-Cath 4Fr catheters, an extensive experiment was conducted using four formulations:

Lock Solution Control (30% ethanol, 4% sodium citrate)
30% ethanol, 4% sodium citrate, with 0.2% Polysorbate 80
30% ethanol, 4% sodium citrate, with 0.2% Pluronic F68
a lock solution of 30% ethanol, 4% sodium citrate with 0.5% Polysorbate 20 and 1% of Glycerol and three different types of silicone catheters: Per-Q-Cath 4Fr, Broviac 4.2Fr, and Hickman 10Fr. The goal of this study was to evaluate the effect of these formulations on the pressure for three different types of silicone catheters after 14 days in saline baths @37° C. Catheters were divided into three groups and tested in three baths filled with saline @37° C. Catheters were refilled with fresh formulations after each round of 14 days (total three rounds of 14 days each).

Results indicated that catheters filled with a lock solution of 30% ethanol, 4% sodium citrate with 0.5% Polysorbate 20 and 1% of Glycerol formulation had the lowest pressure measurements. Formulation with 30% ethanol, 4% sodium citrate, with Polysorbate 80 also performed well.

Another approach that was considered to improve the performance of the lock formulation was to increase the percentage of the additives. Based on the prior results, three formulations were selected:

30% ethanol, 4% sodium citrate with 0.5% Polysorbate 20 and 1.5% Glycerol
30% ethanol, 4% sodium citrate with 2% Glycerol
30% ethanol 4% sodium citrate with 2% Polysorbate 80

Results from the first round of 14 days are presented in Table 3.

TABLE 3

Pressure measurements of catheters subjected to in vitro testing filled with formulations with 2% additives.

| Sample | Description | Pressure (mmHg) 1$^{st}$ round of 14 days |
|---|---|---|
| 28-1H | Hickman with 30% ethanol, 4% sodium citrate with 0.5% Polysorbate 20 and 1.5% Glycerol | w-<20 b-<20 r-<20 |
| 28-2H | Hickman with 30% ethanol, 4% sodium citrate with 2% Glycerol | w-40 b-<20 r-<20 |
| 28-3H | Hickman with 30% ethanol 4% sodium citrate with 2% Polysorbate 80 | w-28 b-80 r-<20 |
| 28-1B | Broviac with 30% ethanol, 4% sodium citrate with 0.5% Polysorbate 20 and 1.5% Glycerol | 60 |
| 28-2B | Broviac with 30% ethanol, 4% sodium citrate with 2% Glycerol | 52 |
| 28-3B | Broviac with 30% ethanol 4% sodium citrate with 2% Polysorbate 80 | 58 |
| 28-1P | Per-Q-Cath with 30% ethanol, 4% sodium citrate with 0.5% Polysorbate 20 and 1.5% Glycerol | <20 |
| 28-2P | Per-Q-Cath with 30% ethanol, 4% sodium citrate with 2% Glycerol | <20 |
| 28-3P | Per-Q-Cath with 30% ethanol 4% sodium citrate with 2% Polysorbate 80 | 42 |
| 1A-H | Hickman with 30% ethanol, 4% sodium citrate with 0.5% Polysorbate 20 and 1.5% Glycerol | w-<20 b-30 r-<20 |
| 2A-H | Hickman with 30% ethanol, 4% sodium citrate with 2% Glycerol | w-36 b-26 r-<20 |
| 3A-H | Hickman with 30% ethanol 4% sodium citrate with 2% Polysorbate 80 | w-<20 b-<20 r-<20 |
| 1B-H | Hickman with 30% ethanol, 4% sodium citrate with 0.5% Polysorbate 20 and 1.5% Glycerol | w-<20 b-22 r-<20 |
| 2B-H | Hickman with 30% ethanol, 4% sodium citrate with 2% Glycerol | w-46 b-50 r-<20 |
| 3B-H | Hickman with 30% ethanol 4% sodium citrate with 2% Polysorbate 80 | w-130 b-<20 r-<20 |
| 1A-B | Broviac with 30% ethanol, 4% sodium citrate with 0.5% Polysorbate 20 and 1.5% Glycerol | <20 |

TABLE 3-continued

Pressure measurements of catheters subjected to in vitro testing filled with formulations with 2% additives.

| Sample | Description | Pressure (mmHg) 1st round of 14 days |
|---|---|---|
| 2A-B | Broviac with 30% ethanol, 4% sodium citrate with 2% Glycerol | <20 |
| 3A-B | Broviac with 30% ethanol 4% sodium citrate with 2% Polysorbate 80 | 42 |
| 1B-B | Broviac with 30% ethanol, 4% sodium citrate with 0.5% Polysorbate 20 and 1.5% Glycerol | 30 |
| 2B-B | Broviac with 30% ethanol, 4% sodium citrate with 2% Glycerol | 28 |
| 3B-B | Broviac with 30% ethanol 4% sodium citrate with 2% Polysorbate 80 | 92 |
| 1-P | Per-Q-Cath with 30% ethanol, 4% sodium citrate with 0.5% Polysorbate 20 and 1.5% Glycerol | 34 |
| 2-P | Per-Q-Cath with 30% ethanol, 4% sodium citrate with 2% Glycerol | 24 |
| 3-P | Per-Q-Cath with 30% ethanol 4% sodium citrate with 2% Polysorbate 80 | 105 |

Note
Hickman has three lumens indicated by white (w), blue (b), and red (r), which indicate the respective size of each lumen.

Results from the first measurements are in favor for the formulations with Glycerol.

While the disclosure has been described in terms of specific embodiments, it is evident in view of the foregoing description that numerous alternatives, modifications and variations will be apparent to those skilled in the art. Accordingly, the disclosure is intended to encompass all such alternatives, modifications and variations which fall within the scope and spirit of the disclosure.

What is claimed is:

1. A catheter locking method comprising: introducing a locking composition into a lumen of the implantable catheter, wherein the locking composition comprises:
   ethanol;
   an anti-coagulant comprising sodium citrate; and
   an excipient that is liquid at room temperature, wherein the excipient comprises one or more of glycerol, polysorbate-20, polysorbate-80, polyethylene glycol-100, polyethylene glycol-200, polyethylene glycol-300, polyethylene glycol-400, poloxomer 124, macrogol 15 hydroxy stearate, polyoxyl 35 castor oil, and t-octylphenoxypolyethoxyethanol, the amount of the excipient being less than the amount of the anti-coagulant and being sufficient to inhibit crystallization of the sodium citrate.

2. The method of claim 1, the locking composition comprising at least about 4% sodium citrate.

3. The method of claim 1, further comprising an anti-microbial compound.

4. The method of claim 3, the antimicrobial compound anti-microbial including one or more of taurolidine, triclosan, chlorhexidine, gentamicin, vancomycin, and combinations thereof.

5. The method of claim 4, the locking composition comprising at least about 4% sodium citrate.

6. The method of claim 1, the excipient being present in an amount ranging from about 0.5%-2% by weight of the locking composition.

7. The method of claim 1, the excipient comprising one or more of glycerol, a polysorbate, a glycol, and a poloxomer.

8. The method of claim 1, the anti-coagulant further comprising one or more of riboflavin, ethylene diamine tetraacetic acid, a heparin, and citric acid.

9. The method of claim 1, the locking composition further comprising one or more lower alcohols other than ethanol.

10. A catheter locking method comprising: introducing a locking composition into a lumen of the implantable catheter, wherein the locking composition comprises:
    a lower alcohol;
    an anti-coagulant comprising sodium citrate; and
    an excipient that is liquid at room temperature, wherein the excipient comprises one or more of glycerol, polysorbate-20, polysorbate-80, polyethylene glycol-100, polyethylene glycol-200, polyethylene glycol-300, polyethylene glycol-400, poloxomer 124, macrogol 15 hydroxy stearate, polyoxyl 35 castor oil, and t-octylphenoxypolyethoxyethanol, the amount of the excipient being sufficient to inhibit crystallization of the sodium citrate.

11. The method of claim 10, the locking composition comprising at least about 4% sodium citrate.

12. The method of claim 10, further comprising an anti-microbial.

13. The method of claim 12, the anti-microbial including one or more of taurolidine, triclosan, chlorhexidine, gentamicin, vancomycin, and combinations thereof.

14. The method of claim 13 the locking composition comprising at least about 4% sodium citrate.

15. The method of claim 10, the excipient being present in an amount ranging from about 0.5%-2% by weight of the locking composition.

16. The method of claim 10, the excipient comprising at least one of glycerol, a polysorbate, a glycol, and a poloxomer.

17. The method of claim 10, the anti-coagulant further comprising one or more of riboflavin, ethylene diamine tetraacetic acid, a heparin, and citric acid.

18. The method of claim 10, the lower alcohol comprising one or more of ethanol, propanol, isopropanol, and butanol.

* * * * *

UNITED STATES PATENT AND TRADEMARK OFFICE
CERTIFICATE OF CORRECTION

PATENT NO. : 10,507,269 B2  
APPLICATION NO. : 16/373850  
DATED : December 17, 2019  
INVENTOR(S) : Lecon Woo et al.

Page 1 of 1

It is certified that error appears in the above-identified patent and that said Letters Patent is hereby corrected as shown below:

In the Specification

At Column 3, Line 64 (approx.), "Poloxomer" is replaced with "Poloxamer".

In the Claims

In Claim 1 (Column 7, Line 45 (approx.)), "poloxomer" is replaced with "poloxamer";

In Claim 3 (Column 8, Line 2 (approx.)), "compound" is removed;

In Claim 4 (Column 8, Line 3 (approx.)), "antimicrobial compound" is removed;

In Claim 7 (Column 8, Line 13 (approx.)), "poloxomer" is replaced with "poloxamer";

In Claim 10 (Column 8, Line 27 (approx.)), "poloxomer" is replaced with "poloxamer"; and In Claim 16 (Column 8, Lines 45-46 (approx.)), "poloxomer" is replaced with "poloxamer".

Signed and Sealed this  
Eighteenth Day of February, 2020

Andrei Iancu  
*Director of the United States Patent and Trademark Office*